(12) United States Patent
Merino et al.

(10) Patent No.: US 10,071,954 B2
(45) Date of Patent: Sep. 11, 2018

(54) HYDROGEN PEROXIDE-ACTIVATED COMPOUNDS AS SELECTIVE ANTI-CANCER THERAPEUTICS

(71) Applicant: University of Cincinnati, Cincinnati, OH (US)

(72) Inventors: Edward J. Merino, Cincinnati, OH (US); James Mulloy, Cincinnati, OH (US); Anish K. Vadukoot, Cincinnati, OH (US); Mark Wunderlich, Cincinnati, OH (US); Safnas F. Abdulsalam, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 90 days.

(21) Appl. No.: 15/026,442

(22) PCT Filed: Oct. 2, 2015

(86) PCT No.: PCT/US2015/053687
§ 371 (c)(1),
(2) Date: Mar. 31, 2016

(87) PCT Pub. No.: WO2016/054486
PCT Pub. Date: Apr. 7, 2016

(65) Prior Publication Data
US 2016/0318849 A1     Nov. 3, 2016

Related U.S. Application Data

(60) Provisional application No. 62/058,706, filed on Oct. 2, 2014.

(51) Int. Cl.
| | |
|---|---|
| *C07C 233/26* | (2006.01) |
| *A61K 31/167* | (2006.01) |
| *A61K 45/06* | (2006.01) |
| *A61K 31/4468* | (2006.01) |
| *A61K 31/704* | (2006.01) |
| *A61K 31/7068* | (2006.01) |
| *C07D 211/58* | (2006.01) |

(52) U.S. Cl.
CPC .......... *C07C 233/26* (2013.01); *A61K 31/167* (2013.01); *A61K 31/4468* (2013.01); *A61K 31/704* (2013.01); *A61K 31/7068* (2013.01); *A61K 45/06* (2013.01); *C07D 211/58* (2013.01)

(58) Field of Classification Search
CPC ................................................... C07C 233/36
See application file for complete search history.

(56) References Cited

U.S. PATENT DOCUMENTS

| | | |
|---|---|---|
| 5,021,478 A | 6/1991 | Ravichandran et al. |
| 6,037,367 A | 3/2000 | Christenson, IV et al. |
| 2003/0108496 A1 | 6/2003 | Yu et al. |
| 2006/0223761 A1 | 10/2006 | Audia et al. |
| 2013/0230542 A1 | 9/2013 | Merino et al. |

OTHER PUBLICATIONS

Pinedo et al. (2000).*
McMahon et al. (2000).*
Vadukoot, Anish K. et al, "Design of a hydrogen peroxide-activatable agent that specifically targets cancer cells," Bioorganic & Medicinal Chemistry 22 (2014) 6885-6892.

* cited by examiner

*Primary Examiner* — Paul V Ward
(74) *Attorney, Agent, or Firm* — Dinsmore & Shohl LLP

(57) ABSTRACT

Provided are compounds according to the following Formula I:

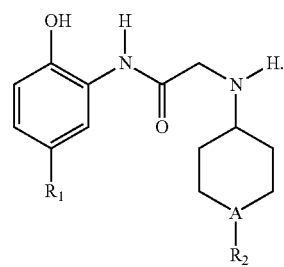

Formula I

The Formula I compounds are activated in the presence of hydrogen peroxide and are therefore selective anti-cancer therapeutics for cancers associated with elevated reactive oxygen species (ROS). Also provided are methods and pharmaceutical compositions for treating cancers associated with increased ROS.

17 Claims, 8 Drawing Sheets

HYDROGEN PEROXIDE-ACTIVATED COMPOUNDS AS SELECTIVE ANTI-CANCER THERAPEUTICS

CROSS REFERENCE TO RELATED APPLICATIONS

This application claims priority to U.S. Provisional Application Ser. No. 62/058,706, filed Oct. 2, 2014, which application is hereby incorporated by reference in its entirety.

TECHNICAL FIELD

The presently disclosed subject matter relates to compounds and methods for treating cancer. More particularly, the presently disclosed subject matter relates to therapeutic compounds that are activated by and specifically target cancer cells associated with elevated levels of reactive oxygen species (ROS), particularly hydrogen peroxide. Pharmaceutical compositions and methods of using the compounds to treat ROS-associated cancers are also described.

BACKGROUND OF THE INVENTION

A challenge in the design of anti-cancer therapeutic drugs is the general toxicity of such drugs to proliferating cells, including a percentage of normal cells. A ubiquitous class of anti-cancer therapeutics includes compounds that modify, bind to, and inhibit the synthesis of DNA. This class lacks selectivity, leading to high levels of intolerable side effects stemming from the modification or interaction of DNA in non-cancerous, highly replicating cells. Such off-target effects limit tolerated doses and, hence, decreases efficacy.

Various strategies are currently under development with the goal of enhancing chemotherapy selectivity for cancer cells. For example, one strategy involves attaching therapeutic agents to active transport scaffolds such that biodistribution of the therapeutic agent is selective for cancer cells. Other approaches involve antibody use, nanoparticles, enzymatic activation, and the like.

Many forms of cancer, and in particular ROS-associated cancers, have low survival rates, primarily due to high relapse rates. For example, in the United States, 44,600 new cases of leukemia, a ROS-associated cancer, were diagnosed in 2011, with a five-year survival rate of 57%. One of the deadliest forms of leukemia, acute myeloid leukemia (AML), accounted for 12,950 of those cases and 9,050 deaths.

A need remains for additional anti-cancer therapeutics, particularly those which target cancer cells with higher selectivity.

SUMMARY OF THE INVENTION

Disclosed herein are novel anti-cancer compounds that are activated by ROS, and in particular hydrogen peroxide, providing compounds that are selective for cancers associated with elevated ROS. In one embodiment, a compound according to Formula I for the treatment of cancer is provided:

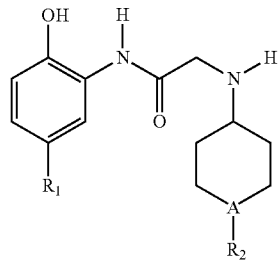

Formula I wherein:
$R_1$ is selected from the group consisting of OH and $NHR_3$, wherein $R_3$ is selected from the group consisting of H and substituted or unsubstituted straight or branched $C_1$-$C_8$ alkyl;

$R_2$ is selected from the group consisting of H, $NHR_4$, $C(=O)R_5$, and substituted or unsubstituted straight or branched $C_1$-$C_8$ alkyl, wherein $R_4$ and $R_5$ are each independently selected from the group consisting of H, substituted or unsubstituted straight or branched $C_1$-$C_8$ alkyl, substituted or unsubstituted straight or branched $C_2$-$C_8$ alkenyl, and substituted or unsubstituted straight or branched $C_2$-$C_8$ alkynyl; and A is selected from the group consisting of C and N.

In another embodiment, a method of reducing proliferative capacity in a cell is provided, the method comprising contacting the cell with an effective amount of a compound according to Formula I.

In another embodiment, a method of treating a cancer associated with elevated ROS is provided, the method comprising administering to a subject in need thereof an effective amount of a compound according to Formula I.

In another embodiment, a pharmaceutical composition for the treatment of a cancer associated with elevated ROS is provided, the pharmaceutical composition comprising: (a) a therapeutically effective amount of a compound according to claim 1; and (b) a pharmaceutically-acceptable carrier.

These and other objects, features, embodiments, and advantages will become apparent to those of ordinary skill in the art from a reading of the following detailed description and the appended claims.

BRIEF DESCRIPTION OF THE DRAWINGS

FIG. 3A shows the proposed oxidation pathway of compound 1. Oxidation provides a quinone. In the presence of a nucleophile, like N-acetylcysteine, a conjugate addition reaction followed by an elimination results in the aromatic NAC-2 species. FIG. 3B shows $^1$H-NMR data for compound 2 (upper panel) and compound NAC-2 (lower panel). The proton shifts at approximately 8 and 7 ppm on the lower panel do not show multiplicity, indicating that N-acetylcysteine has added to C5. FIG. 3C shows HPLC analysis of reaction products in the absence of NAC (grey) and upon addition of NAC (black). The peak at 11.2 mins was identified as the NAC-2 adduct. FIG. 3D shows hydrogen peroxide increases the rate of conversion of 1 into 2 to 0.6 min-1, an enhancement of at least 60-fold. FIG. 3E shows FTMS of NAC-2.

FIG. 4A shows a proposed oxidation pathway of compound 14, whereby oxidation of compound 14 leads to cyclization or dimerization (not shown) to produce 14-ox. This oxidation product can potentially reduce, giving 14-red. FIG. 4B shows that 14-ox can cyclize at either C1 or C3, giving products of distinct molecular weight. FIG. 4C shows HPLC analysis of two distinct products: 14 (lower grey) and its oxidation (upper black). Compound 14 in the absence of oxygen and peroxide is not oxidized. Two hour exposure to the atmosphere leads to some conversion to 14-ox while hydrogen peroxide converts all 14 in less than 0.1 hours. FIG. 4D shows isolation and MS spectra of 14-ox and 14-red.

FIG. 5A shows the proposed tautomeric structures of 14. FIG. 5B shows the oxidation product can potentially reduce, giving 14-red (top NMR panel). 14-ox can be predicted from the $^1$H-NMR of the equilibrated species (bottom NMR panel). FIG. 5C shows HPLC traces of NAC-addition product with 14 (left panel) and ITMS of the NAC adduct (right panel).

FIG. 6A shows the ratio of CD34+ normal blood stem cell to AML activity of select synthesized agents and natural products piperlongumine (PLG) and parthenolide (PTL). FIG. 6B shows viability of AML (black) and CD34+ normal blood stem cells (grey) in the presence of compound 14.

FIG. 8A shows that addition of 20 µM 14 to AML cells leads to a time dependent loss in cellular ROS levels as measured by DCF fluorescence assay. FIG. 8B shows electrophilic molecules, like compound 14, are detected by a loss in concentration of the sensor protein KEAP1 ($p<0.05$ in all cases). A representative image of a gel imaged on a Li-cor Odeyssey® imager is shown (right panel). The upper band is the amount of electrophilic sensor protein KEAP1, while the lower band is a loading control via detection of ACTB. Beta actin does not change upon treatment of 14 in these AML cells. It is known that KEAP1 is modified by electrophilic sensors leading its degradation and activation of response proteins. A bar plot shows the ratio of KEAP1 to ACTB in the presence and absence of 2 µM 14 (left panel). Addition of 14 leads to a statistically significant reduction in KEAP1, indicating that 14 elicits a response in AML cells.

DETAILED DESCRIPTION

A hallmark of many cancer cells is elevated levels of reactive oxygen species (ROS) such as superoxide, hydrogen peroxide, hydroxyl radical, and singlet oxygen. Overexpression of oncoproteins such as Ras has been linked to elevated ROS, as has the overexpression of oxidases that drive survival signals in hypoxic solid tumors. Excess ROS benefits malignant cells, increasing mutagenic DNA damage that leads to activated oncogenes and enhanced formation of adaptive advantages. Leukemia cells often have mutations that result in permanent activation of the oncogene k-Ras, a GTPase that regulates growth signals. Permanent Ras activation increases ROS levels and increases expression of proteins that allow cancer cell growth. Further, leukemic cells often have elevated NAD(P)H oxidase 2 levels compared to healthy blood cells. NAD(P)H oxidases generate ROS when performing their function. Oxidases are important in cancer progression because these enzymes have been shown to inhibit apoptosis, inactivate tumor suppressors via ROS, and enhance angiogenesis. Excess ROS further benefits malignant cells by upregulating redox-regulated growth and survival factors.

Certain ROS-associated cancer agents are currently employed in cancer therapy. For example, arsenic trioxide and doxorubicin are known to generate ROS as part of their mechanisms of action. Initial strategies to utilize elevated ROS in cancer cells focused on the inactivation of the anti-oxidant glutathione. Newer ROS-associated approaches use prodrugs that possess a hydrogen peroxide-sensitive boronic ester or agents that release toxic metabolites.

It has now been discovered that elevated ROS associated with certain cancers can be leveraged to design anti-cancer therapeutics that are activated by ROS and selectively target cancer cells, thus limiting off-target effects.

Figure 1:
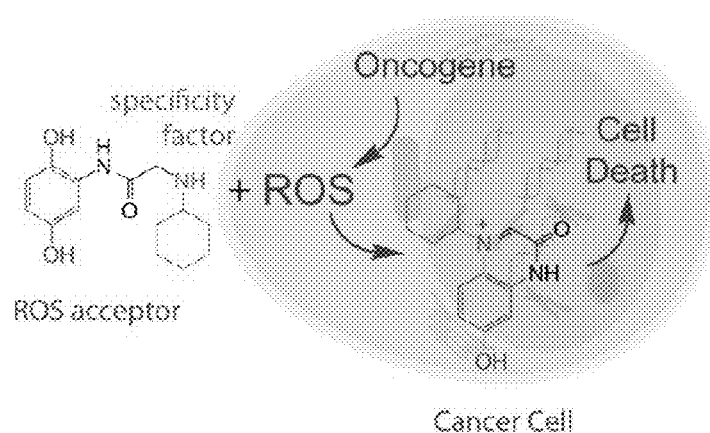
FIG. 1 shows the reaction by which an exemplary compound of the present invention is activated by hydrogen peroxide. The hydrogen peroxide-activatable agent reacts via formation of a conjugate addition product.

The compounds disclosed herein employ an activation strategy, whereby the compounds are locked in an inactive state until unlocked by a cancer cell-specific phenotype that converts the agent into a cytotoxic DNA modifying agent. Elevated levels of hydrogen peroxide convert more of the compounds into highly cytotoxic DNA-modifying agents. The activation strategy enhances the selectivity of the agents, rendering them less capable of exerting a cytotoxic mechanism of action on normal cells. FIG. 1 shows the process by which an exemplary compound of the present invention is activated by hydrogen peroxide. While not desiring to be bound by theory, it is believed that hydrogen peroxide facilitates conjugate addition after oxidation, since the agents possess an amine and its tether ortho to the hydroxyl group of the hydroquinone. This would then cause the electrophilic center to be C5, thus facilitating hydrogen peroxide-activated conjugation, utilizing quinone chemistry.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

The terms "Reactive oxygen species" or "ROS" refer to chemically reactive molecules containing oxygen. ROS include, for example, superoxide, hydrogen peroxide, hydroxyl radical, and singlet oxygen.

The term "cancer" as used herein refers to diseases caused by uncontrolled cell division and the ability of cells to metastasize, or to establish new growth in additional sites. The terms "malignant," "malignancy," "neoplasm," "tumor," and variations thereof refer to cancerous cells or groups of cancerous cells.

In certain embodiments, "cancer" refers to a cancer associated with elevated levels of ROS. Specific types of cancer associated with elevated ROS include, but are not limited to, leukemia, including acute myeloid leukemia, acute lymphoblastic leukemia, plasmacytoma, myeloma, myelogenous leukemia, acute lymphocytic leukemia, acute promyelocytic leukemia, and multiple myeloma; renal cancer; and cancers of the central nervous system.

As used herein the term "alkyl" refers to $C_1$-$C_{20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, ethynyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 9 to about 20 carbon atoms, e.g., 9, 10, 11, 12, 13, 14, 15, 16, 17, 18, 19, or 20 carbon atoms. In certain embodiments, "alkyl" refers, in particular, to $C_{1-8}$ alkyls or $C_2$-$C_8$ alkenyls or alkynyls.

Alkyl groups can optionally be substituted (a "substituted alkyl") with one or more alkyl group substituents, which can be the same or different. The term "alkyl group substituent" includes but is not limited to substituted or unsubstituted alkyl, alkoxyl, halo, hydroxyl (—OH), cyano (—CN), carboxyl, carboxyl ester, aryloxyl, alkylthio, arylthio, aralkyloxyl, aralkylthio, alkoxycarbonyl, oxo, acyl, and cycloalkyl. There can be optionally inserted along the alkyl chain one or more heteroatoms, such as oxygen, sulfur or substituted or unsubstituted nitrogen atoms, wherein the nitrogen substituent is hydrogen, lower alkyl (also referred to herein as "alkylaminoalkyl"), cycloalkyl, or aryl. In a specific embodiment, alkyl substitutions are selected from the group consisting of alkoxyl, halo, hydroxyl (—OH), cyano (—CN), carboxyl, carboxyl ester, substituted or unsubstituted alkyl, and combinations thereof.

Thus, as used herein, the term "substituted alkyl" includes alkyl groups, as defined herein, in which one or more atoms or functional groups of the alkyl group are replaced with another atom or functional group, including for example, alkoxyl, halo, hydroxyl (—OH), cyano (—CN), carboxyl, carboxyl ester, and substituted or unsubstituted alkyl.

As used herein, the term "cyloalkyl" refers to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with a substituent as defined herein. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl. In certain embodiments, "cycloalkyl" comprises ($C_3$-$C_8$) cycloalkyl.

As used herein, the term "aza" refers to a heterocyclic ring structure containing at least one nitrogen atom. Specific examples of aza groups include, but are not limited to, pyrrolidine, piperidine, quinuclidine, pyridine, pyrrole, indole, purine, pyridazine, pyrimidine, and pyrazine.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl."

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

The term "amino" refers to the —$NH_2$ group.

The term "carbonyl" refers to the —(C=O)— group.

The term "carboxyl" refers to the —COOH group. The term "carboxyl ester" refers to the —C(O)OR' group.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "cyano" refers to the —CN group.

When the term "independently selected" is used, the substituents being referred to (e.g., R groups, such as groups $R_4$ and $R_5$), can be identical or different.

II. Compounds

Figure 2:
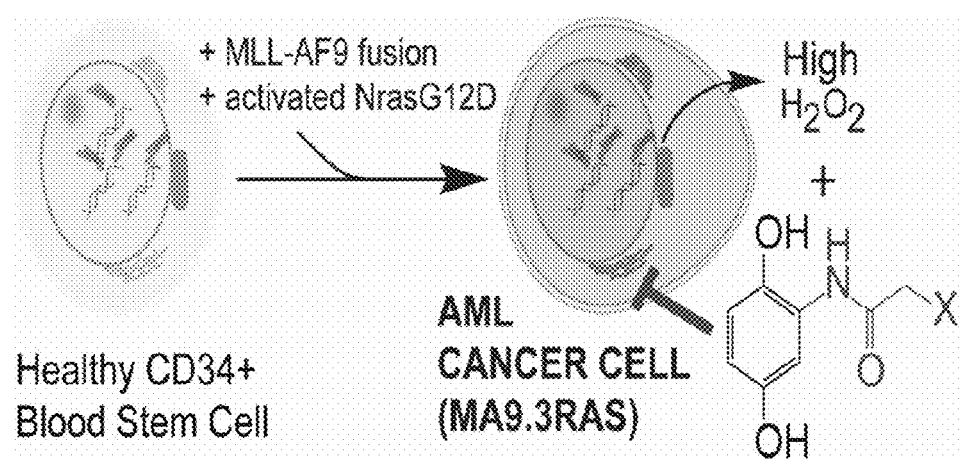
FIG. 2 shows the design of hydrogen peroxide activatable anti-cancer agents based on conjugate addition. A linker on an oxidation-prone hydroquinone is installed to enforce conjugate addition after hydrogen peroxide oxidation. X represents an alpha substituent of the acetamide.

At the biochemical level, ROS molecules catalyze formation of disulfide bonds or sulfinic acids to alter proteins and subsequent activity responsible for growth and angiogenesis. For example, tumor cells from approximately 60% of patients with AML show elevated ROS, in some cases, a 100-fold elevation is observed. This increased ROS provides an opportunity for exploitation via a pro-drug strategy—i.e., molecules that are unreactive until oxidized by hydrogen peroxide. Once oxidized, the molecules are capable of a conjugate addition reaction. The instant compounds migrate the amine and its tether ortho to the hydroxyl group of the hydroquinone (see FIG. 2). The electrophilic center generated upon hydrogen peroxide activation becomes C5, which change facilitates hydrogen peroxide-activated conjugate addition, utilizing quinone chemistry.

The presently disclosed subject matter provides ROS-activated compounds according to the following Formula I:

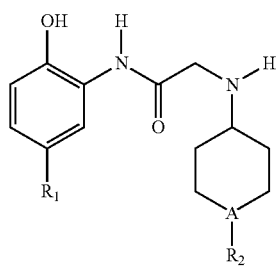

Formula I wherein:

$R_1$ is selected from the group consisting of OH and $NHR_3$, wherein $R_3$ is selected from the group consisting of H and substituted or unsubstituted straight or branched $C_1$-$C_8$ alkyl;

$R_2$ is selected from the group consisting of H, $NHR_4$, $C(=O)R_5$, and substituted or unsubstituted straight or branched $C_1$-$C_8$ alkyl, wherein $R_4$ and $R_5$ are each independently selected from the group consisting of H, substituted or unsubstituted straight or branched $C_1$-$C_8$ alkyl, substituted or unsubstituted straight or branched $C_2$-$C_8$ alkenyl, and substituted or unsubstituted straight or branched $C_2$-$C_8$ alkynyl; and A is selected from the group consisting of C and N.

In a specific embodiment, $R_1$ is OH. In another specific embodiment, $R_1$ is $NH_2$. In another specific embodiment, A is C and $R_2$ is H.

In certain embodiments, $R_1$ is $NHR_3$ and $R_3$ is selected from the group consisting of substituted or unsubstituted methyl, ethyl, propyl, isopropyl, acetyl, and $C(=O)R_6$, wherein $R_6$ is selected from the group consisting of lower alkyl, lower alkenyl, lower alkynyl, aryl, arylalkyl, cycloalkyl, and amine, and wherein $R_3$ is optionally substituted with one or more halo or alkyl substitutions.

In other embodiments, $R_1$ is OH, A is C, and $R_2$ is selected from the group consisting of substituted or unsubstituted methyl, ethyl, propyl, isopropyl, butyl, isobutyl, tert-butyl, and pentyl, and wherein $R_2$ is optionally substituted with one or more halo or alkyl substitutions.

In a specific embodiment, when A is N, then $R_2$ is $C(=O)R_5$, wherein $R_5$ is selected from the group consisting of H and substituted or unsubstituted methyl, ethyl, propyl, isopropyl, butyl, isobutyl, tert-butyl, pentyl, ethenyl, propenyl, ethynyl, and propynyl, and wherein $R_5$ is optionally substituted with one or more halo or alkyl substitutions.

In a further embodiment, the hydroxyl moiety at the C2 position on the phenyl ring my be optionally replaced with an amine group, such as $NH_2$ or $NHR_7$, wherein $R_7$ is selected from the group consisting of substituted or unsubstituted straight or branched $C_1$-$C_8$ alkyl, alkenyl, or alkynyl.

In another embodiment, the $R_1$ moiety is selected from the group consisting of thiol and SR8, wherein R8 is selected from the group consisting of substituted or unsubstituted straight or branched $C_1$-$C_8$ alkyl, alkenyl, or alkynyl.

Compounds of Formula I are suitable for use as anti-cancer therapeutics for cancers associated with elevated reactive oxygen species. In a specific embodiment, the cancer is selected from the group consisting of leukemia, renal cancer, and cancers of the central nervous system. In a more specific embodiment, the leukemia is selected from the group consisting of acute myeloid leukemia, acute lymphoblastic leukemia, plasmacytoma, myeloma, myelogenous leukemia, acute lymphocytic leukemia, acute promyelocytic leukemia, and multiple myeloma.

In some embodiments, the compound of Formula I can be used to contact a cell or cell extract having elevated ROS. In some embodiments, the compound can be used to contact a tissue, tissue extract, or other biologically derived sample, such as a blood sample. In some embodiments, the compound of Formula I can be used to contact a cell having elevated ROS in vivo, wherein the cell is present in a living subject, such as a mammal or bird. In some embodiments, the mammal is a human. By activating in the presence of ROS such as hydrogen peroxide, the compound of Formula I or a pharmaceutical formulation thereof can be used to modify the DNA of a cell exhibiting elevated ROS, thereby resulting in cytotoxicity of the target cell.

III. Pharmaceutical Formulations

The compounds of Formula I and pharmaceutically acceptable salts thereof are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral or intravenous administration as discussed in greater detail below. Also, the presently disclosed subject matter provides such active compounds that have been lyophilized and that can be reconstituted to form pharmaceutically acceptable formulations (including formulations pharmaceutically acceptable in humans) for administration.

The therapeutically effective dosage of any specific active compound, the use of which is within the scope of embodiments described herein, will vary somewhat from compound to compound, and subject to subject, and will depend upon the condition of the subject and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the presently disclosed methods, pharmaceutically active compounds as described herein can be administered orally as a solid or as a liquid, or can be administered intramuscularly or intravenously as a solution, suspension, or emulsion. Alternatively, the compounds or salts also can be administered intravenously or intramuscularly as a liposomal suspension.

Pharmaceutical formulations suitable for intravenous or intramuscular injection are further embodiments provided herein. The pharmaceutical formulations comprise compounds of Formula I described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula I or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula I or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods of Inhibiting Cell Proliferation and Treating Cancer with Ros-Activated Compounds The presently disclosed subject matter provides methods and compositions for inhibiting cell proliferation. In particular, the presently disclosed subject matter provides methods of specifically targeting cancer cells associated with increased concentrations of reactive oxygen species (ROS). Thus, the presently disclosed subject matter provides a method of treating diseases, including cancer, which are associated with increased production of ROS.

In some embodiments, the methods for inhibiting cell proliferation or treating a cancer comprise administering to a subject in need thereof an active compound as described herein. These active compounds, as set forth above, include the compounds of Formula I, their corresponding prodrugs, and pharmaceutically acceptable salts of the compounds and prodrugs. In some embodiments, the active compound is present in a pharmaceutical formulation as described hereinabove.

The presently disclosed compounds can provide therapy for a wide variety of tumors and cancers including leukemia, renal cancers, central nervous system (CNS) cancers, and other cancers associated with increased production of ROS.

An "effective amount" is defined herein in relation to the treatment of cancers is an amount that will decrease, reduce, inhibit, or otherwise abrogate the growth of a cancer cell or tumor. In some embodiments, the compound of Formula I can be delivered regionally to a particular affected region or regions of the subject's body. In some embodiments, wherein such treatment is considered more suitable, the compound of Formula I can be administered systemically. For example, the compound can be administered orally or intravenously.

In addition, it will be appreciated that therapeutic benefits for the treatment of cancer can be realized by combining treatment with a ROS-activated compound or other compound of the presently disclosed subject matter with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination. For example, the ROS-activated compound can be combined with other agents and therapeutic regimens that are effective at reducing tumor size (e.g., radiation, surgery, chemotherapy, hormonal treatments, and or gene therapy). Further, in some embodiments, it can be desirable to combine the ROS-activated compound with one or more agents that treat the side effects of a disease or the side effects of one of the therapeutic agents, e.g., providing the subject with an analgesic, or agents effective to stimulate the subject's own immune response (e.g., colony stimulating factor).

A variety of additional therapeutic agents, also described as "anti-neoplastic" agents or "chemotherapeutic agents" can be used in combination with one or more of the ROS-activated compounds of the presently described subject matter. Such compounds include, but are not limited to, alkylating agents, antibiotics, antimetabolites, DNA intercalators, protein synthesis inhibitors, inhibitors of DNA or RNA synthesis, DNA base analogs, topoisomerase inhibitors, anti-angiogenesis agents, telomerase inhibitors or telomeric DNA binding compounds, and P-glycoprotein inhibitors.

For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents such as distamycin and netropsin, also can be combined with compounds of the presently disclosed subject matter in pharmaceutical compositions.

Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the ROS-activated compounds of the presently disclosed subject matter to provide a suitable cancer treatment.

Platinum-containing anti-cancer drugs such as cisplatin, carboplatin, and oxaliplatin can also be combined with the ROS-activated compounds of the presently disclosed subject matter to provide a suitable cancer treatment.

Inhibitors of P-glycoproteins, such as zosuquidar, tariquidar, and taniquidar, are also suitable anti-cancer therapeutics that can be combined with the ROS-activated compounds presently disclosed.

Additional chemotherapeutic agents suitable for combination with the ROS-activated compounds disclosed herein include gemtuzumab, all-trans retinoic acid (ATRA), and sorafenib.

In a more specific embodiment, therapeutic agents that can be used in a combination treatment with a ROS-activated compound of the presently disclosed subject matter include cytarabine, doxorubicin, cisplatin, chlorambucil, cladribine, zosuquidar, gemtuzumab, arsenic trioxide, sorafenib, and the like.

Combination treatments involving a ROS-activated compound and another therapeutic agent, such as another chemotherapeutic agent can be achieved by contacting cells with the ROS-activated compound and the other agent at the same time. Such combination treatments can be achieved by contacting the cell with a single composition or pharmacological formulation that includes both agents, or by contacting the cell with two distinct compositions or formulations, at the same time, wherein one composition includes the ROS-activated compound and the other includes the other agent.

Alternatively, treatment with the ROS-activated compound can precede or follow treatment with the other agent by intervals ranging from minutes to weeks. In embodiments where the other agent and the ROS-activated compound therapy are applied separately to the cell, one would generally ensure that a significant period of time did not expire between the time of each delivery, such that the agent and the ROS-activated compound treatment would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the ROS-activated compound or of the other agent will be desired.

In another embodiment, a ROS-activated compound of the presently disclosed subject matter or another anti-cancer compound being used in combination with the ROS-activated compound is either combined with or covalently bound to a cytotoxic agent bound to a targeting agent, such as a monoclonal antibody (e.g., a murine or humanized monoclonal antibody). It will be appreciated that the latter combination can allow the introduction of cytotoxic agents into cancer cells with greater specificity. Thus, the active form of the cytotoxic agent (i.e., the free form) will be present only in cells targeted by the antibody.

Additional cancer treatments also can be used in combination with administration of a ROS-activated compound. For example, a ROS-activated compound of the presently disclosed subject matter can be used as part of a treatment course further involving attempts to surgically remove part or all of a cancerous growth. For instance, a ROS-activated compound of the presently disclosed subject matter can be administered after surgical treatment of a subject to treat any remaining neoplastic or metastasized cells. Treatment with a ROS-activated compound of the presently disclosed subject matter also can precede surgery, in an effort to shrink the size of a tumor to reduce the amount of tissue to be excised, thereby making the surgery less invasive and traumatic.

Treating cancer with a ROS-activated compound of the presently disclosed subject matter can further include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

A combination therapy also can involve immunotherapy directed at tumor antigen markers that are found on the surface of tumor cells. Treatment of a cancer with a ROS-activated compound of the presently disclosed subject matter can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN-II, BRCA1, VHL, FCC, MCC, ras, myc, neu, raf, erb, src, fms, jun, trk, ret, gsp, hst, bcl, and abl, which are often mutated versions of their normal cellular counterparts in cancerous tissues.

The ROS-activated compounds of the presently disclosed subject matter can be tested to measure their ability to inhibit growth of cancer cells, to induce apoptosis of the cancer cells, to reduce tumor burden, and to inhibit metastases. For example, one can measure cell growth according to the MTT assay. Growth assays as measured by the MTT assay are well known in the art. In the MTT assay, cancer cells are incubated with various concentrations of anti-cancer compound, and cell viability is determined by monitoring the formation of a colored formazan salt of the tetrazolium salt, 3-(4,5-dimethylthiazol-2-yl)-2,5-diphenyltetrazolium bromide (MTT). Other known assays for measuring cell death and or cell proliferation can also be employed.

In vivo testing can be performed using a mouse xenograft model, for example, in which MA9.3 AML cancer cells are grafted onto nude mice, in which mice treated with a compound of Formula I are expected to have tumor masses that, on average, increase for a period following initial dosing, but will shrink in mass with continuing treatment. In contrast, mice treated with a control (e.g., DMSO) are expected to have tumor masses that continue to increase. Additional methods of measuring the anti-neoplastic effects of the presently disclosed compounds are described further, hereinbelow, in the Examples.

EXAMPLES

The presently disclosed subject matter will be described more fully hereinafter with reference to the accompanying Examples, in which representative embodiments are shown. The presently disclosed subject matter can, however, be embodied in different forms and should not be construed as limited to the embodiments set forth herein.

Example 1

Hydrogen Peroxide-Activated Compounds

Table 1 sets forth hydrogen peroxide-activated compounds of the present invention, together with their $IC_{50}$ values corresponding to a 50% reduction in the percent of CD34+ selected human umbilical cord blood cells (UCB) and MA9.3 RAS AML cells.

Cells were seeded at a density of $4 \times 10^4$ cells/well in a 96-well plate and incubated at 37° C. overnight. Then cells were treated for 48 hours with indicated concentrations of freshly dissolved compounds. The plates were centrifuged at 1500×g for 5 minutes at 4° C. to pellet the cells and the medium containing compounds was discarded; fresh medium containing 20 µL of MTT (5 mg/mL) was added to each well and incubated for an additional 4 h. The medium was removed. After adding 200 µL of DMSO to each well, the optical densities at 575 nm were determined. Cytotoxicity data are expressed as $IC_{50}$ values obtained from the fit to a four parameter sigmoid using the graphing software KaleidaGraph (Synergy Software). All $R^2$ values were greater than 0.98 and standard errors of the three replicates were less than 20%.

TABLE 1

Hydrogen Peroxide-Activated Compounds

| Compound Reference Number | Compound | $IC_{50}$ against MA9.3RAS AML cells (µM) | $IC_{50}$ against UCB (µM) |
|---|---|---|---|
| 14 | 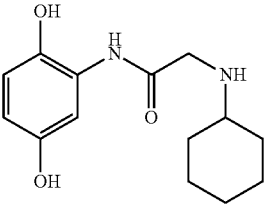 [SMILES: O=C(CNC1CCCCC1)Nc1cc(O)ccc1O]<br>2-(cyclohexylamino)-N-(2,5-dihydroxyphenyl)acetamide | 2 ± 1 | 20 ± 2 |

TABLE 1-continued

Hydrogen Peroxide-Activated Compounds

| Compound Reference Number | Compound | IC$_{50}$ against MA9.3RAS AML cells (μM) | IC$_{50}$ against UCB (μM) |
|---|---|---|---|
| 15 | 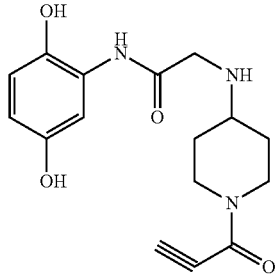 [SMILES: C#CC(=O)N1CCC(NCC(=O)Nc2cc(O)ccc2O)CC1]<br>N-(5-amino-2-hydroxyphenyl)-2-(1-propioloylpiperidin-4-ylamino)acetamide | 3 ± 1 | 40 ± 6 |
| 16 | 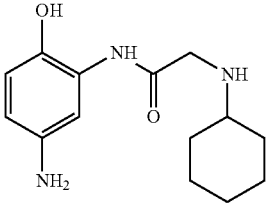<br>N-(5-amino-2-hydroxyphenyl)-2-(cyclohexylamino)acetamide | 3 ± 1 | 55 ± 4 |

Example 2

Synthesis of ROS-Activated Compounds

Synthesis of Compounds

1. Synthesis of 2-(cyclohexylamino)-N-(2,5-dihydroxyphenyl)acetamide

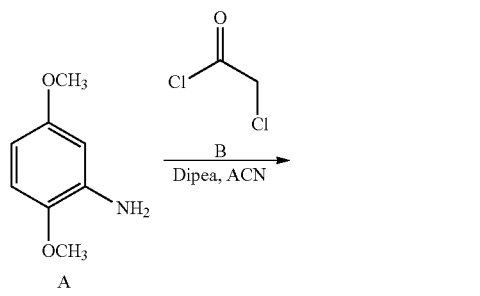

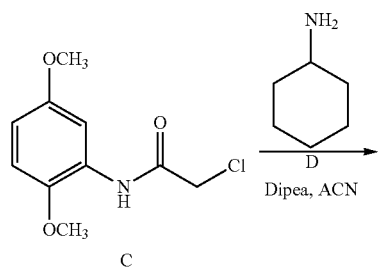

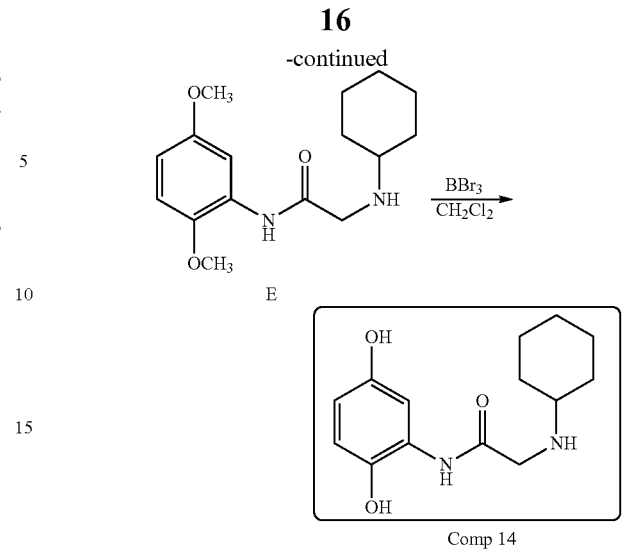

Step 1: Synthetic Route for Compound C

To a solution of compound A (8.0 g, 52.22 mmoles) in ACN (30.0 mL) was added DIPEA (20.01 mL, 114.88 mmoles), followed by dropwise addition of compound B (4.98 mL, 62.67 mmoles) under argon atmosphere. After the addition was complete, the reaction was stirred at room temperature (rt) for 1 hour. The completion of the reaction was monitored by thin layer chromatography (TCL). The reaction mixture was concentrated, purified by column chromatography (20% EtOAc:hexanes) to isolate the required compound as brown solid (10.23 g, 85.32%). $^1$H-NMR (CDCl$_3$, 400 MHz) δ 8.97 (br s, 1H), 8.08 (d, J=3.2 Hz, 1H), 6.84 (d, J=8.8 Hz, 1H), 6.64 (dd, J=3.2, 8.8 Hz, 1H), 4.21 (s, 2H), 3.89 (s, 3H), 3.80 (s, 3H).

Step 2: Synthetic Route for Compound E

To a solution of compound C (1.0 g, 4.35 mmoles) and compound D (0.6 mL, 5.23 mmoles) in Acetonitrile (15.0 mL) was added di-isopropylethyl amine (2.28 mL, 13.05 mmoles) drop-wise. After the addition was complete the reaction was refluxed for 12 hours. The completion of the reaction was monitored by TLC. The reaction mixture was concentrated, purified by column chromatography (10% MeOH:CH$_2$Cl$_2$) to isolate the required compound as an brown oil (0.70 g, 55%). $^1$H-NMR (CDCl$_3$, 400 MHz) δ 10.06 (s, 1H), 8.18 (d, J=3.09 Hz, 1H), 6.82 (d, J=8.86 Hz, 1H), 6.59 (dd, J=3.08, 8.87 Hz, 1H), 3.87 (s, 3H), 3.81 (s, 3H), 3.42 (s, 2H), 2.47-2.42 (m, 1H), 1.96-1.91 (m, 2H), 1.77-1.61 (m, 3H), 1.29-1.10 (m, 5H).

Step 3: Synthetic Route for Compound 14

To a solution of compound E (0.5 g, 1.710 mmoles) in anhydrous dichloromethane (15.0 mL) was added boron tribromide (0.972 mL, 10.26 mmoles) drop-wise at −78° C. and stirred for 2 h at the same temperature. The completion of the reaction was monitored by TLC. The reaction mixture was quenched by slow addition of saturated NaHCO$_3$ solution until the reaction mixture became basic and was extracted into dichloromethane (10 mL), concentrated and purified by column chromatography (15% MeOH:CH$_2$Cl$_2$) to isolate the required compound as an white solid (0.53 g, 90%). $^1$H-NMR (CD$_3$OD, 400 MHz) δ 7.59 (s, 1H), 6.70-6.68 (m, 1H), 6.44-6.41 (m, 1H), 3.65 (s, 2H), 2.71 (t, J=10.14 Hz, 1H), 2.03-1.99 (m, 2H), 1.83-1.80 (m, 2H), 1.68 (d, J=12.05 Hz, 1H), 1.36-1.24 (m, 5H). $^{13}$C-NMR (CD$_3$OD, 400 MHz) δ 163.57 (C), 149.71 (C), 140.68 (C), 125.36 (C), 115.54 (CH), 111.65 (CH), 109.16 (CH), 57.21 (CH), 45.54 (CH$_2$), 28.83 (CH$_2$), 24.61 (CH$_2$), 24.11 (CH$_2$).

HRMS (ESI) for [MH]$^+$ calculated: 265.15467, observed: 265.15469

2. Synthesis of N-(5-amino-2-hydroxyphenyl)-2-(1-propioloylpiperidin-4-ylamino)acetamide

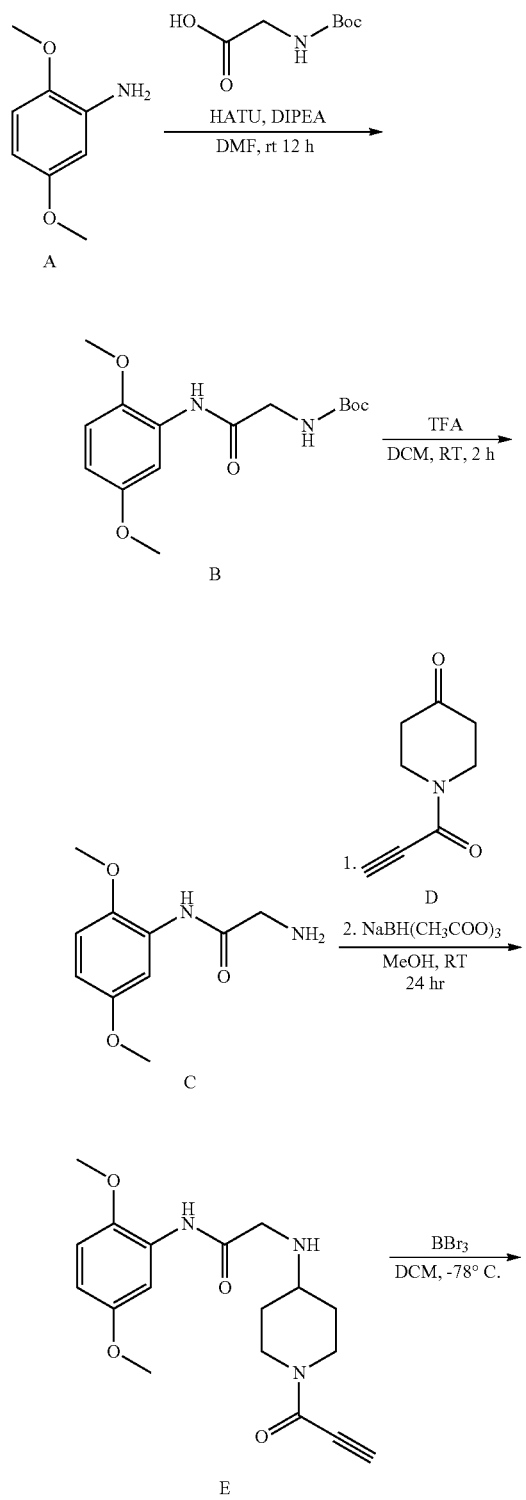

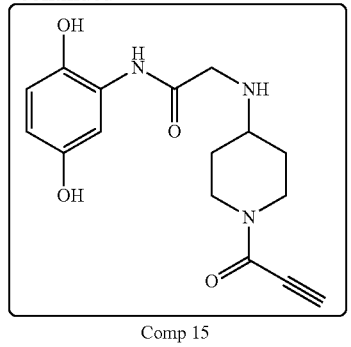

Comp 15

Step 1: Synthetic Route for Compound B

Boc-glycine (1.0 g, 6.0 mmol) was first dissolved in 20 mL DMF. HATU (4.0 g, 13.0 mmol) was added and the mixture was stirred for 15 mins. Compound A was added to it dropwise and was stirred for another 30 mins. This was followed by addition of DIPEA (4.14 mL, 23.76 mmoles) into the mixture and reaction was stirred overnight. Reaction mixture was extracted into EtOAc using water work up, organic layer was concentrated and column purified to obtain required product as brown solid (1.07 g, 41.6%). $^1$H-NMR (CDCl$_3$, 400 MHz) δ 8.45 (s, 1H), 7.92 (s, 1H), δ=6.59 (d, J=6.6 Hz, 1H), δ=6.39 (d, J=6.6 Hz, 1H), δ=3.8 (2H, s), δ=3.61 (3H, s), δ=3.59 (3H, s), 1.36 (9H, s)

Step 2: Synthetic Route for Compound C

Compound B (1.5 g) was dissolved in 10 ml of DCM and Trifluoroacetic acid (3.0 ml) was added dropwise with stirring. The reaction was stirred over night. The reaction mixture was quenched using saturated NaHCO$_3$ solution and pH was adjusted to 8.0. This was followed by extracting the compound into EtOAc using EtOAc:H$_2$O workup. The organic layer was dried over sodium sulfate and concentrated to obtain required compound as brown solid (0.180 g, 74.2). $^1$H-NMR (400 Hz, CDCl3) δ 9.72 (s, 1H), δ 8.17 (s, 1H), 6.80 (d, J=6.8 Hz, 1H), 6.58 (m, 1H), 3.85 (s, 3H), 3.78 (s, 3H), 3.5 (s, 2H).

Step 3: Synthetic Route for Compound E

To solution of compound C (0.250 g, 1.2 mmoles) in MeOH (8.0 mL), compound D (0.150 g, 1.0 mmol) was added dropwise and the reaction was stirred for 30 mins. This was followed by addition of NaBH(OAC)$_3$ (0.650 mg, 3.0 mmol) portion wise and the reaction was stirred overnight. Crude reaction mixture was carefully quenched using water and compound extracted into EtOAc. Organic layer was then concentrated, and column purified to obtain the required compound as an oily liquid (0.20 g, 90.4%). $^1$H-NMR (400 MHz, CDCl$_3$) δ 9.80 (s, 1H), 8.12 (d, J=8.11 Hz, 1H), 7.28 (d, J=6.8 Hz, 1H), 6.79 (d, J=6.8 Hz, 1H), 6.58 (d, J=6.8 Hz, 1H), 3.83 (s, 3H), 3.77 (s, 3H), 3.62 (m, 4H), 3.18 (m, 2H), 2.56 (m, 2H), 2.41 (m, 2H).

Step 4: Synthetic Route for Compound 15

To a solution of compound E (0.282 g, 0.920 mmoles) in anhydrous dichloromethane (15.0 mL) was added boron tribromide (0.525 mL, 5.523 mmoles) drop-wise at −78° C. and stirred for 2 h at the same temperature. The completion of the reaction was monitored by TLC. The reaction mixture was quenched by slow addition of saturated NaHCO$_3$ solution till the reaction mixture becomes basic and was extracted into dichloromethane (10 mL), concentrated and purified by column chromatography (15% MeOH:CH$_2$Cl$_2$) to isolate the required compound as an yellow brown solid (0.078 g, 30.4%)$^1$H-NMR (400 MHz, DMSO-d6) δ 10.57 (s, 1H), 8.86 (s, 1H), 6.68 (d, J=6.68 Hz, 1H), 6.41-6.36 (m, 2H), 4.93 (s, 1H). 3.77-3.67 (m, 2H), 3.55-3.49 (m, 1H), 3.40 (s, 1H), 3.36-3.22 (m, 2H), 2.09-1.45 (m, 5H) $^{13}$C-NMR (101 MHz, DMSO) δ 161.90 (C), 150.19 (C), 126.35 (C), 123.98 (C), 112.51 (CH), 109.43 (C), 102.53 (C), 86.05 (C), 68.61 (C), 47.79 (CH$_2$), 27.99 (CH$_2$), 26.03 (CH), −0.00 (CH$_2$).

3. Synthesis of -(5-amino-2-hydroxyphenyl)-2-(cyclohexylamino)acetamide

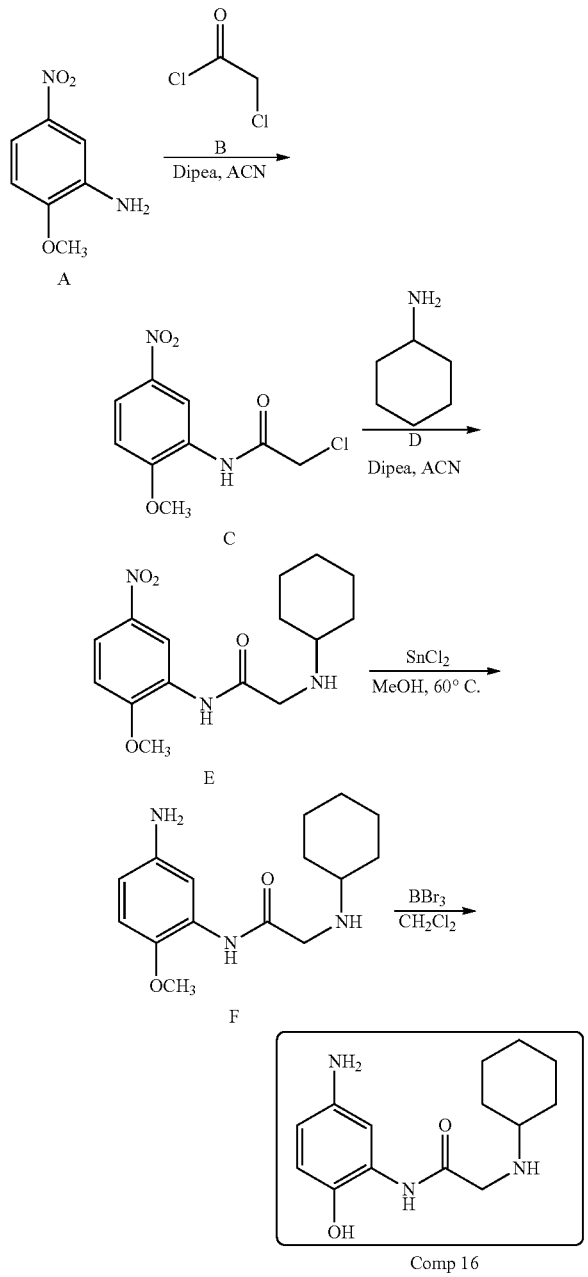

Step 1: Synthetic Route for Compound C

To a solution of compound A (0.50 g, 2.973 mmoles) in ACN (10.0 mL) was added DIPEA (1.57 mL, 8.92 mmoles), followed by dropwise addition of compound B (0.354 mL, 8.920 mmoles) under argon atmosphere. After the addition was complete the reaction was stirred at rt for 1 hour. The completion of the reaction was monitored by TLC. The reaction mixture was concentrated, purified by column chromatography (20% EtOAc:Hexanes) to isolate the required compound as brown solid (0.653 g, 89.65%). $^1$H-NMR (DMSO-d$_6$, 400 MHz) δ 9.90 (s, 1H), 8.99 (d, J=2.9 Hz, 1H), 8.07 (dd, J=2.9, 9.1 Hz, 1H), 7.30 (d, J=9.1 Hz, 1H), 4.45 (s, 2H), 4.01 (s, 3H).

Step 2: Synthetic Route for Compound E

To a solution of compound C (0.5 g, 2.044 mmoles) and compound D (0.28 mL, 2.453 mmoles) in Acetonitrile (15.0 mL) was added di-isopropylethyl amine (1.08 mL, 6.132 mmoles) drop-wise. After the addition was complete the reaction was refluxed for 12 hours. The completion of the reaction was monitored by TLC. The reaction mixture was concentrated, purified by column chromatography (10% MeOH:CH$_2$Cl$_2$) to isolate the required compound as an brown oil (0.396 g, 70%). $^1$H-NMR (CDCl$_3$, 400 MHz) δ 10.19 (s, 1H), 9.33 (d, J=2.8 Hz, 1H), 7.99 (d, J=2.8, 9.0 Hz, 1H), 6.93 (d, J=9.1, Hz, 1H), 4.02 (s, 3H), 3.44 (s, 2H), 2.53-2.36 (m, 1H), 2.01-1.84 (m, 2H), 1.77-1.61 (m, 3H), 1.37-1.10 (m, 6H).

Step 2: Synthetic Route for Compound F

To a solution of compound E (0.25 g, 0.813 mmoles) in MeOH (10.0 mL) was added SnCl$_2$ (0.771 g, 4.067 mmoles) and reaction refluxed for 3 hours. The reaction mixture was dried down and quenched with sat. NaHCO$_3$. Organic compound was extracted into EtOAc (10 mL×3) and column purified to isolate the required compound as an black oily liquid (0.190 g, 93.59%). $^1$H-NMR (CDCl$_3$, 400 MHz) δ 9.99 (s, 1H), 7.922 (d, J=2.8 Hz, 1H), 6.71 (d, J=8.6 Hz, 1H), 6.37 (dd, J=2.8, 8.5 Hz, 1H), 3.82 (s, 3H), 3.40 (s, 2H), 2.50-2.34 (m, 1H), 1.92 (d, J=12.7 Hz, 2H), 1.78-1.68 (m, 2H), 1.37-1.00 (m, 6H).

Step 3: Synthetic Route for Compound 16

To a solution of compound E (0.06 g, 0.216 mmoles) in anhydrous dichloromethane (15.0 mL) was added boron tribromide (0.082 mL, 0.865 mmoles) drop-wise at −78° C. and stirred for 2 h at the same temperature. The completion of the reaction was monitored by TLC. The reaction mixture was quenched by slow addition of saturated NaHCO$_3$ solution until the reaction mixture becomes basic and was extracted into dichloromethane (10 mL), concentrated and purified by column chromatography (15% MeOH:CH$_2$Cl$_2$) to isolate the required compound as an yellow brown solid (0.034 g, 59.7%). $^1$H-NMR (CD$_3$OD, 400 MHz) δ 7.53 (d, J=2.7 Hz, 1H), 6.62 (d, J=8.5 Hz, 1H), 6.38 (dd, J=2.7. 8.5 Hz, 1H), 3.33 (s, 2H), 2.39 (t, J=10.3 Hz, 1H), 1.95-1.81 (m, 2H), 1.72-1.58 (m, 2H), 1.64-1.52 (m, 1H), 1.34-1.01 (m, 5H).
$^{13}$C-NMR (CD$_3$OD, 400 MHz) δ 173.16 (C), 141.34 (C), 140.62 (C), 127.57 (C), 116.84 (CH), 113.52 (CH), 110.14 (CH), 58.55 (CH), 58.50 (CH$_2$), 34.34 (CH$_2$), 27.14 (CH$_2$), 26.08 (CH$_2$).

Example 3

Structure-Function Analysis of Hydrogen Peroxide-Activated Compounds

PLG (piperlongumine) and PTL (parthenolide) are recently identified natural reactive molecules that extend life in mouse models of aggressive cancers. Both these natural products modify protein targets through a conjugate addition reaction.

Compounds 1-14 of Table 2 were synthesized:

TABLE 2

IC$_{50}$ Values for Structure-Function Analysis of Test Compounds 1-14

| | Structure | IC$_{50}$ (μM) |
|---|---|---|
| 1 | (structure) | 6 ± 1 |
| 2 | (structure) | 21 ± 4 |
| 3 | (structure) | >100 |
| 4 | (structure) | >100 |
| 5 | (structure) | >100 |
| 6 | (structure) | 35 ± 5 |
| 7 | (structure) | 16 ± 2 |

TABLE 2-continued

IC$_{50}$ Values for Structure-Function Analysis of Test Compounds 1-14

| | Structure | IC$_{50}$ (μM) |
|---|---|---|
| PLG | (structure) | 2 ± 1 |
| 8 | (structure) | 12 ± 3 |
| 9 | (structure) | 13 ± 2 |
| 10 | (structure) | 3 ± 1 |
| 11 | (structure) | 5 ± 1 |
| 12 | (structure) | 18 ± 2 |
| 13 | (structure) | 9 ± 2 |

TABLE 2-continued

IC$_{50}$ Values for Structure-Function Analysis of Test Compounds 1-14

| | Structure | IC$_{50}$ (μM) |
|---|---|---|
| 14 | (2,5-dihydroxyphenyl)-NH-C(=O)-CH$_2$-NH-cyclohexyl | 2 ± 1 |
| PTL | parthenolide structure | 3 ± 1 |

Compound 14 has an IC$_{50}$ value of 2 μM against AML cancer cells. Upon hydrogen-peroxide induced oxidation, 14 formed a bicyclic ring that equilibrated between an electrophilic oxidized and a reduced relatively stable state. Hydrogen peroxide activated the compound by more than 150-fold. Incubation with N-acetylcysteine leads to formation of a conjugate addition. Cellular testing showed that the AML model system possesses more ROS than normal blood stem cells from healthy donors and the addition of 14 consumes ROS as part of its mechanism. Importantly, 14 is 11-fold selective and activates AML cells electrophilic defense system.

Figure 3:
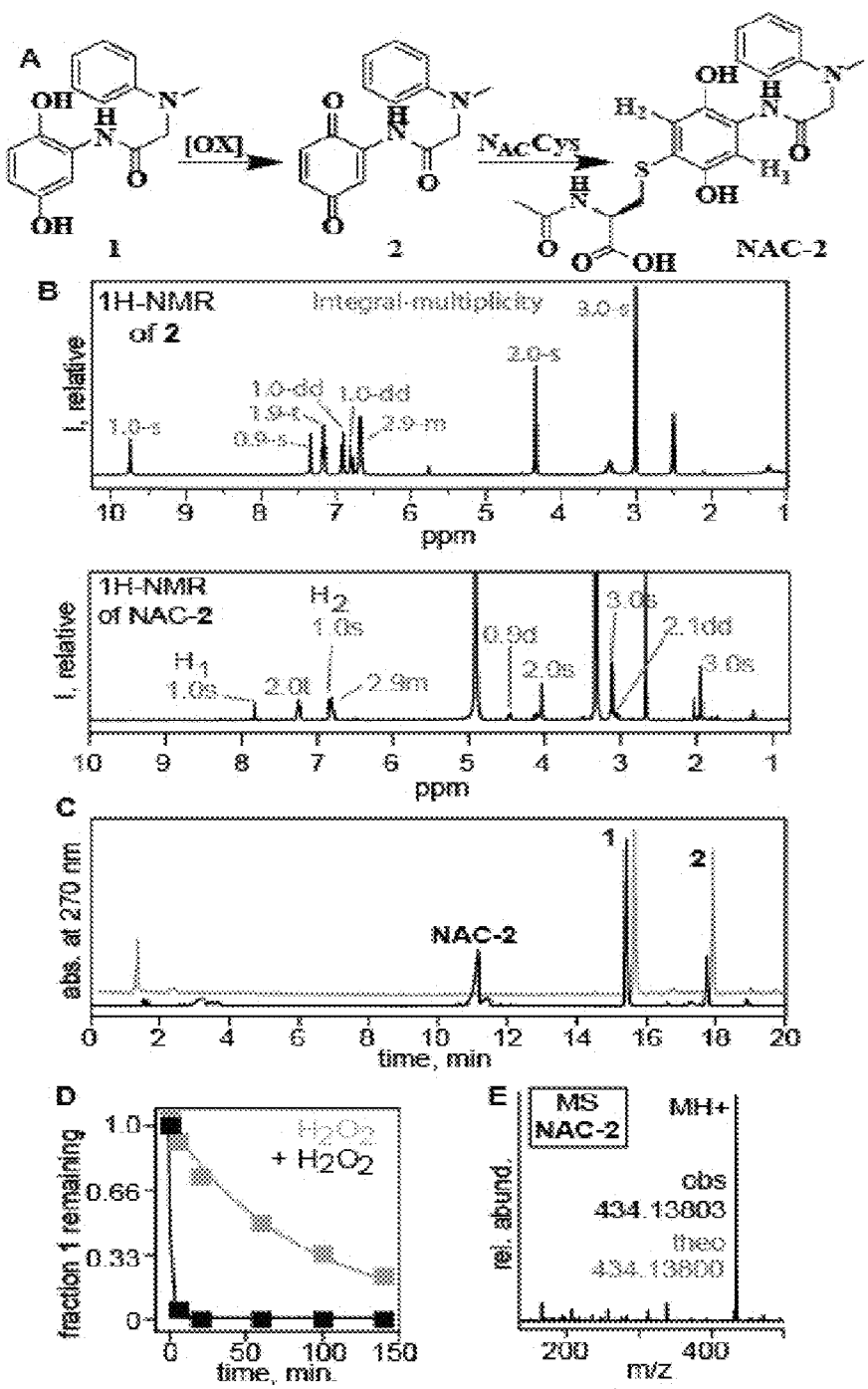
FIG. 3 shows reactivity data for compound 1.

To begin the molecular design process, compound 1 was synthesized and its oxidation examined. Two aspects of the design were of concern based on previously published studies of similar compounds. First, oxidation could form either the 1,4-quinone or an α-substituted-N-arylacetamide. Second, because of the many tautomers, several positions could serve as the electrophilic center. To identify the oxidation product of 1, (diacetoxyiodo)benzene was used as a model oxidizer (FIG. 3B). The product after two-electron and concurrent two-proton oxidation was isolated and found to be compound 2 based on $^1$H-NMR. $^1$H-NMR showed a broad singlet at 9.75 ppm confirming the presence of amide proton and the formation of 1,4 quinone rather than α-substituted-N-arylacetamide. The next step in the reaction is the conjugate addition. As a test reaction, the substrate N-acetylcysteine was incubated in dimethylsulfoxide (DMSO) along with 2 for 2 hours. After isolation, NAC-2 was characterized by $^1$H-NMR (FIG. 3B). The spectrum revealed that addition occurred at C5. Singlets were observed at 7.83 ppm for H$_1$ and 6.85 ppm for H$_2$. If the addition had happened at C6, doublets due to meta coupling between H$_3$ and H$_5$ protons would have been present in the spectrum. FIG. 3A shows the proposed reaction pathway: oxidation, conjugate addition, and regeneration of aromaticity.

To mimic cellular addition, 1 was incubated in PBS with limiting N-acetylcysteine and the products were analyzed by HPLC (FIG. 3C). The limiting N-acetylcysteine was necessary due to the formation of multiple addition products, since addition of a thiol to the aromatic ring makes further oxidation and addition easier. Compound 1 was converted to 2 in the absence of exogenous oxidant at a rate of 0.011±0.002 min$^{-1}$ (FIG. 3D, grey line), which leads to approximately 50% conversion in one hour. ROS-induced activation of 1 was then assessed. In the presence of 10 mM H$_2$O$_2$, a ten-fold excess, the rate of conversion was enhanced by more than 60-fold to 0.6±0.1 min$^{-1}$. Once 2 was formed, N-acetylcysteine was added and NAC-2 was rapidly produced (FIG. 3C, black line) as confirmed by FTMS (FIG. 3E). Thus, 1 is activated by ROS, indicating that this agent will react with biomolecules in cells under higher oxidative stress.

Structural components within 1 were then probed to determine effect on potency. The goal was to obtain activity that matched the two natural products, PTL and PLG, which show efficacy in tumor xenografts in mice. As a model system cytotoxicity of synthesized agents in the MA9.3RAS AML cell line was examined. These cells are transformed CD34$^+$ human blood stem cells engineered to express both an MLL-AF9 fusion protein and the common oncogene NrasG12D. Culturing was accomplished as previously described by Wunderlich, et al., Leukemia 24(10):1785-88 (2010). The molecular signatures associated with these cells closely mimic those identified in primary AML patient samples and the MLL-fusion is associated with poor survival. Cytotoxicity studies were performed in triplicates using an MTT cell proliferation assay. All MTT assays were repeated twice.

Compound 1 had an IC$_{50}$ value (i.e., concentration at which only 50% of the AML cells survive) of 6±1 μM. Oxidation within cells was necessary for activity since the IC$_{50}$ of 2 was 21±4 μM. In support of the requirement for cellular oxidation, compound 3, which is not readily oxidized into the corresponding quinone due to the presence of methoxy groups, had an IC$_{50}$ greater than 100 μM. Compounds 4 and 5, each lacking a single phenol at positions 2 and 5, respectively, also had IC$_{50}$ values greater than 100 μM, showing the importance of both hydroxyl groups. Replacement of a hydroxyl group with hydrogen makes oxidization much less favorable. Analysis of these compounds indicated that oxidation was a prerequisite for high activity. Thus, these data indicate that a key requirement in obtaining a cytotoxic compound is the ability of the compound to be oxidized.

Molecular requirements of "X" functionality (α-substituent of the acetamide, FIG. 2) were next assessed in compounds 6-14 (Table 2). In compound 6, the N-methylaniline of 1 was replaced with hydrogen; this substitution reduced the IC$_{50}$ by approximately 6 fold to 35±5 μM. The amine-substituted 7 had an IC$_{50}$ of 16±2 μM, whereas replacement of the N-methylaniline with a hydroxyl group (compound 8) resulted in an IC$_{50}$ of 12±3 μM. We then synthesized a derivative lacking the methyl on the aniline, 9. Compared to compound 1, compound 9 also had a moderate reduction in activity (IC$_{50}$ of 13±2 μM). Two isosteres, 10 and 11, containing a phenol and thiophenol, respectively had greater activity than 9 with IC$_{50}$ values of 3±1 μM and 5±1 μM. The distal aromatic ring was then replaced with alkyl groups. In 12, substitution with an N-methylpropylamine reduced activity to 18±2 μM. Compound 13, an N-methylcyclohexylamine derivative, showed a slight reduction in potency to 9±2 μM compared to 1, but its activity is improved over 12. The most active compound was 14, in which the aromatic ring was replaced with a cyclohexane. Compound 14 had an IC$_{50}$ of 2±1 μM against AML cells. Compound 14 was selected for further chemical and biochemical analysis since it met the criterion of having similar IC$_{50}$ as the two natural products that showed efficacy.

Further structure-activity relationship studies were carried out, using compound 14 as the base structure. Table 3 shows IC$_{50}$ values for test compounds 14-19.

TABLE 3

IC$_{50}$ Values for Structure-Function Analysis of Test Compounds 14-19

| Compound Reference Number | Compound | IC50 (uM) |
|---|---|---|
| 14 | (structure: 2-(cyclohexylamino)-N-(2,5-dihydroxyphenyl)acetamide) | 2 ± 1 |
| 15 | (structure with piperidine-N-acryloyl group) | 3 ± 1 |
| 16 | (structure with NH$_2$ on ring) | 5 ± 2 |
| 17 | (structure with NO$_2$ on ring) | 22 ± 7 |
| 18 | (structure with α-CH$_3$) | 104 ± 2 |
| 19 | (structure with α-cyclohexyl) | 107 ± 1 |

Results from an MTT assay are shown. Cells used were MA9.3 AML cells. These studies indicate that either an amine or a hydroxyl substitution is acceptable at the lower position on the aromatic ring, as observed in the favorable IC$_{50}$ values for compounds 14-16, although NO$_2$ substituted at the same location caused a decrease in efficacy (compound 17). The alpha CH$_2$ did not appear amenable to perturbations, as observed in the decreased IC$_{50}$ values for compounds 18 and 19. The cycloalkyl substituent on the terminal amine was amenable to inclusion of a heteroatom, specifically N, substituted with an alkyl substituent, as observed in the favorable IC$_{50}$ value for compound 15.

Example 4

Chemical Reactivity of Compound 14

Figure 4:
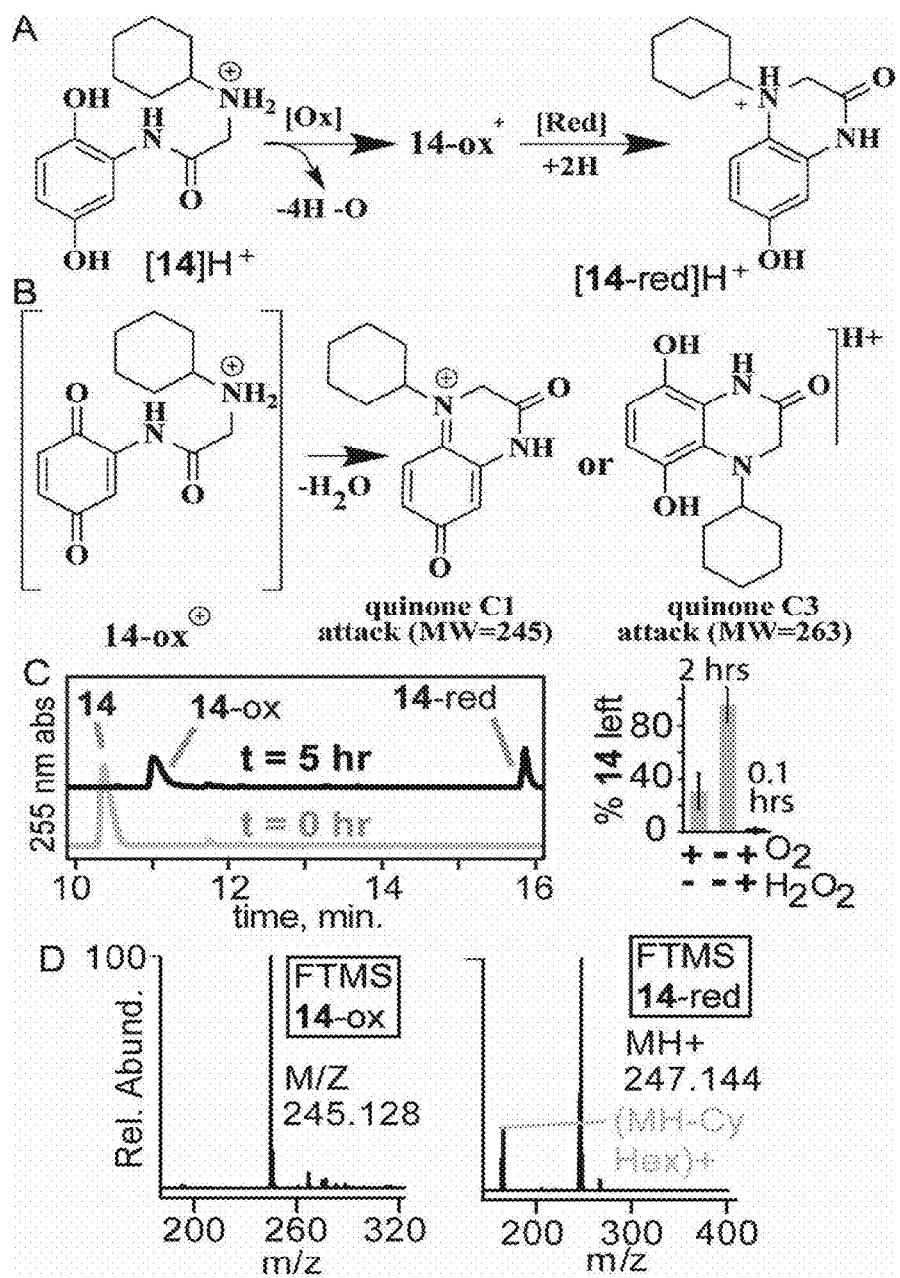
FIG. 4 shows oxidation of compound 14 leads to cyclization.

Chemical reactivity of compound 14 was examined. A potential reaction scheme is shown in FIG. 4A. It was hypothesized that the chemistry of 14 would differ significantly from 1. First, as a secondary aliphatic amine, a possible cyclization reaction upon oxidation was envisioned. The best possibilities for cyclization via amine addition was to C1 or C3 of the phenol to generate a new six-membered ring. Additionally, nucleophilic attack could occur at C2 or by a second molecule to yield a dimer. The two six membered ring possibilities are shown in FIG. 4B.

Representative HPLC chromatograms in the presence and absence of hydrogen peroxide are shown in FIG. 4C (left hand side). Interestingly, by comparing the dark and light grey chromatograms it is observed that two products were formed (11.2 and 15.9 min elution times). These products were produced via both spontaneous and hydrogen-peroxide induced oxidation but not under an argon atmosphere (FIG. 4C right hand side). It was found that only 4±3% of 14 was converted to its oxidation product in two hours under argon atmosphere. Under normal atmosphere the reaction proceeds under pseudo-zero order reaction kinetics with a $t_{1/2}$ of 155±13 min. Importantly, addition of one molar equivalent hydrogen peroxide led to a near instantaneous conversion to the oxidized products. Using the lower limit of $t_{1/2}$ less than 1 min leads to a large rate enhancement. Initially, the two products were isolated and a high-resolution MS was obtained on both. The corresponding FTMS is shown in FIG. 4D. After isolation, it was found that the 14-ox product that eluted at 11.2 min had an elemental composition of $C_{14}H_{17}N_2O_2^+$, m/z 245.148 with an error less than 100 ppb, which inferred oxidation and additionally lost $H_3O^+$. Several tautomers of 14-ox are possible (see FIG. 5A). Importantly, the second product (14-red) that eluted at 15.9 min had an elemental composition of $C_{14}H_{19}N_2O_2^+$, m/z 247.144 with an error less than 100 ppb, which was a reduction of 14-ox.

Figure 5:
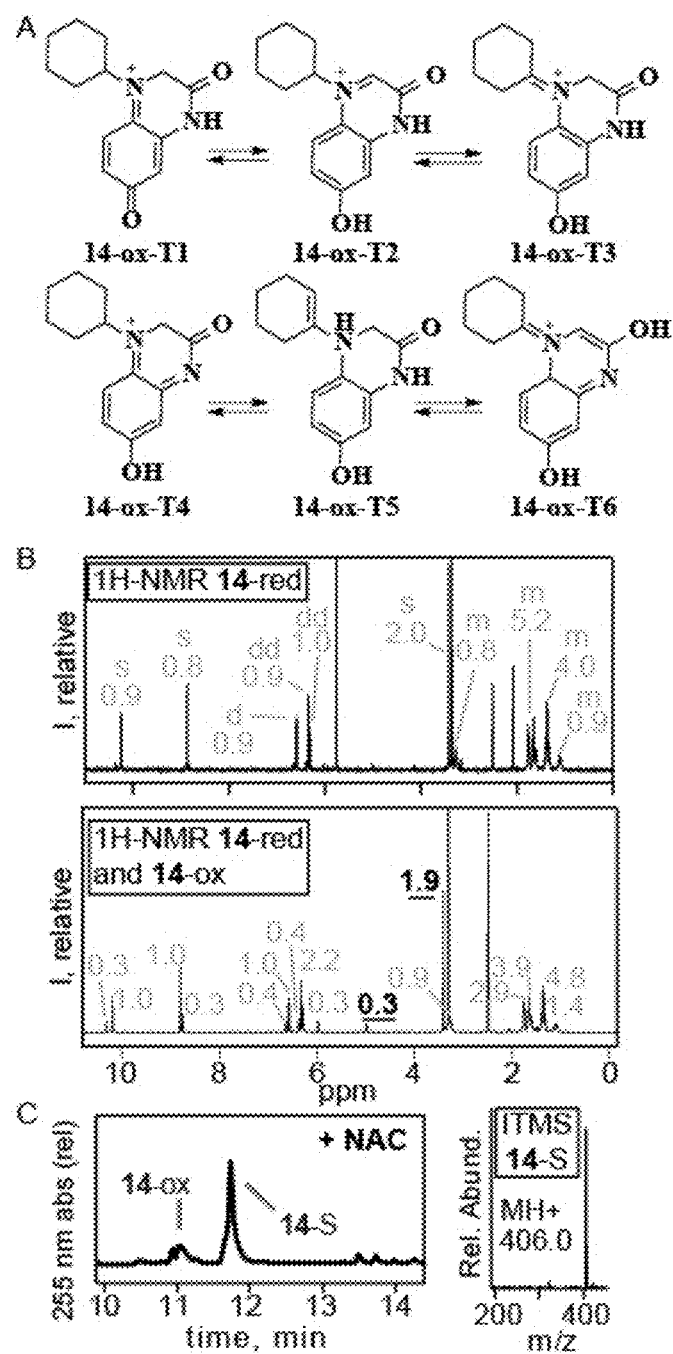
FIG. 5 shows oxidation of compound 14 leads to cyclization.

Several critical questions remained including the tautomeric state and whether thiol could add to 14-ox. FIG. 5A details six key tautomers possible from 14-ox (numbered T1-T6). It was possible to precipitate 14-red from aqueous solutions as neither 14-ox nor 14-red is stable to chromatography or heating. Thus, the structure of 14-red was identified. 14-red was allowed to equilibrate back to 14-ox to identify its structure.

Important proton resonances for 14-red are as follows. Two singlets at δ 10.24 (s, 1H) and δ 8.87 (s, 1H) correspond to the amido proton of the tether and hydroxyl group of the quinone. Aromatic protons showed up at δ6.59 (d, J=9.0 Hz, 1H), δ6.35-6.30 (m, 2H). A singlet at δ3.42 (s, 2H) ppm corresponds to protons on α-carbon next to the carbonyl group. Cyclohexylamine protons showed up at δ3.31-3.21 (m, 1H), δ1.77-1.59 (m, 5H), δ1.40-1.33 (m, 4H), δ 1.11-1.08 (m, 1H). The $^1$H-NMR is consistent with the tautomer shown in FIG. 4A. Importantly, the structure of 14-ox could be assigned by allowing pure 14-red to equilibrate back into a ~25% mixture of 14-ox. This equilibration takes approximately 1 hour. The spectrum was normalized to the most downfield 14-red aromatic shift at δ6.59 ppm. By doing this, it becomes apparent that there is a set of shifts corresponding to 14-red at single proton counts and a smaller set corresponding to 14-ox. There should be a total integration, assuming 25% 14-ox and 75% 14-red of 23.4 proton integration sum between the two species and we observe 23.0, well within error. The proton shifts for the 14-ox are given as follows. Amido protons and phenolic hydroxyl are present as singlets at 10.3 and 8.48 ppm respectively with an integration of 0.3. There are three aromatic protons observed with one doublet that is shifted up-field to δ5.58 ppm since it is adjacent to the cationic site. Since 14-red has a total 11 protons in cyclohexyl ring, then the proton integration sum for both species should be 14.3. They are well accounted for in the spectrum. The most important and defining proton shift is the α-$CH_2$ group (at δ3.39 ppm). There are supposed to be a total of 2.6 proton integration sum combined between 14-red and 14-ox but integrated value is 1.9 (bold and underlined in FIG. 5B, bottom NMR). This indicates that there is no α-$CH_2$ group present in 14-ox. Interestingly, a new shift was observed at δ4.98 ppm (bold and underlined in FIG. 5B, bottom NMR) similar to an allylic proton shift with an intensity of 0.3. Based on this information, 14-ox-T3, 14-ox-T4, 14-ox-T5, and 14-ox-T6 (FIG. 5A) are eliminated as likely structures since they lack this characteristic proton shifts. This leaves the only candidate tautomer as 14-ox-T2. Thus, 14-ox is likely not in a quinone state but in-fact an aromatic bicyclic ring (14-ox-T2).

Reactivity toward nucleophile addition was validated. As before, addition was examined using N-acetylcysteine via HPLC (FIG. 5C). Limiting N-acetylcysteine was necessary due to the formation of multiple addition products as observed in HPLC and MS since the first addition leads to easier oxidation and capture of the next (thiol) nucleophile. When N-acetylcysteine is present, a new product is observed at 12 min (14-S in FIG. 5C). Upon isolation and MS of 14-S a single m/z value of 406.0 by ITMS is observed. Thus, 14 is oxidatively activated and reacts with nucleophiles.

Example 5

Selectivity of Compounds

The selectivity of select compounds was examined by treatment of primary $CD34^+$ normal human blood stem cells. These are untransformed and are genetically similar to MA9.3RAS cells except they lack the MLL-AF9 oncogene and active $Nras^{G12D}$ oncogene. It is essential that reactive agents be selective since off-target reactivity is of great concern. In anti-cancer compounds, a selectivity factor, which in this instance is the ratio between the $IC_{50}$ of normal cells over the $IC_{50}$ of the AML cells, of one log unit is desired. The selectivity factors for selected compounds are given in FIG. 6A. Compound 1 is marginally selective with a ratio of 2.0±0.2. In addition, compound 2 showed similar selectivity. Active compounds, which are isosteres to 1, 10 and 11 also had limited selectivity. Neither compound 6 nor compound 7 were selective, indicating that both linker and nitrogen affect selectivity. Replacement of the aniline of 1 significantly enhanced selectivity. Conversion of the aniline to an alkyl amine led to improved selectivity. Compound 13 had a selectivity factor of 3.8±1.4. Importantly, 14 was highly selective with a ratio of $IC_{50}$ values of 11.5±0.5.

Figure 6:
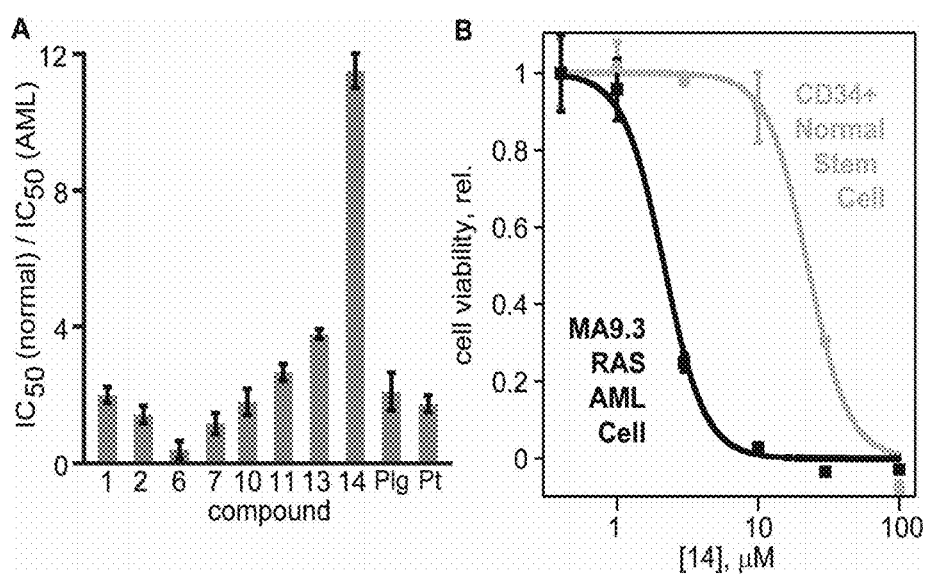
FIG. 6 shows that compound 14 displays highly selective anti-AML activity.

Selectivity of compound 14 was compared to the selectivity of two natural products that show efficacy in tumor xenografts in mice. PLG is thought to be reactive via a conjugate addition reaction leading to a depletion of cellular antioxidant capacity. Thus, selective targeting of cancers with elevated ROS status occurs. Similarly, PTL is a sesquiterpene lactone that utilizes conjugate addition. Table 2 shows that 14 has similar anti-AML activity as both these natural products. PLG has an $IC_{50}$ of 2±1 µM, while PTL has an $IC_{50}$ of 3±1 µM. Strikingly, 14 was more selective than either PLG or PTL in the MA9.3RAS AML cells as their respective selectivity were 3.7±1 and 2.1±0.4. When AML and control cells were treated with compound 14, AML cells were eradicated at a concentration that did not affect viability of normal blood stem cells (FIG. 6B).

Example 6

Model AML Cells Display High ROS Compared to Normal Cells

Figure 7:
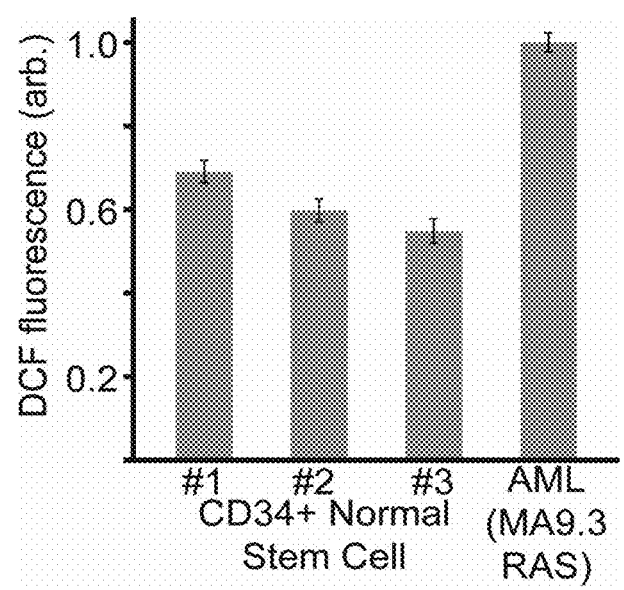
FIG. 7 shows that compound 14 displays ROS-dependent and selective anti-AML activity. Blood stem cells from three healthy donors each show less ROS than the model AML cell line ($p<0.01$ in all cases) as measured by DCF fluorescence assay.

Though it is widely accepted that bulk AML cells have elevated concentrations of reactive oxygen, it was desirable to ensure that the instant models had higher levels of ROS than healthy cells. CD34+ blood stem cells were harvested from three donors. Cells were counted, incubated with 2,7-dihydrodichlorofluorescein (DCF) diacetate, and their respective fluorescence compared after 30 min (FIG. 7). After deacylation, DCF is oxidized by a broad spectrum of ROS species and oxidases. Thus is a marker of general ROS and oxidation within cells. The three CD34+ selected UCB cell populations each derived from different healthy donors referred as #1 through #3 (FIG. 7) had fluorescence intensity of 0.69±0.03 ($p<0.002$), 0.60±0.03 ($p<10^{-6}$), 0.54±0.02 ($p<10^{-6}$) compared to 1.00±0.02 in the AML cell model.

Example 7

Treatment Leads to Lower ROS and Signs of Reactivity

Figure 8:
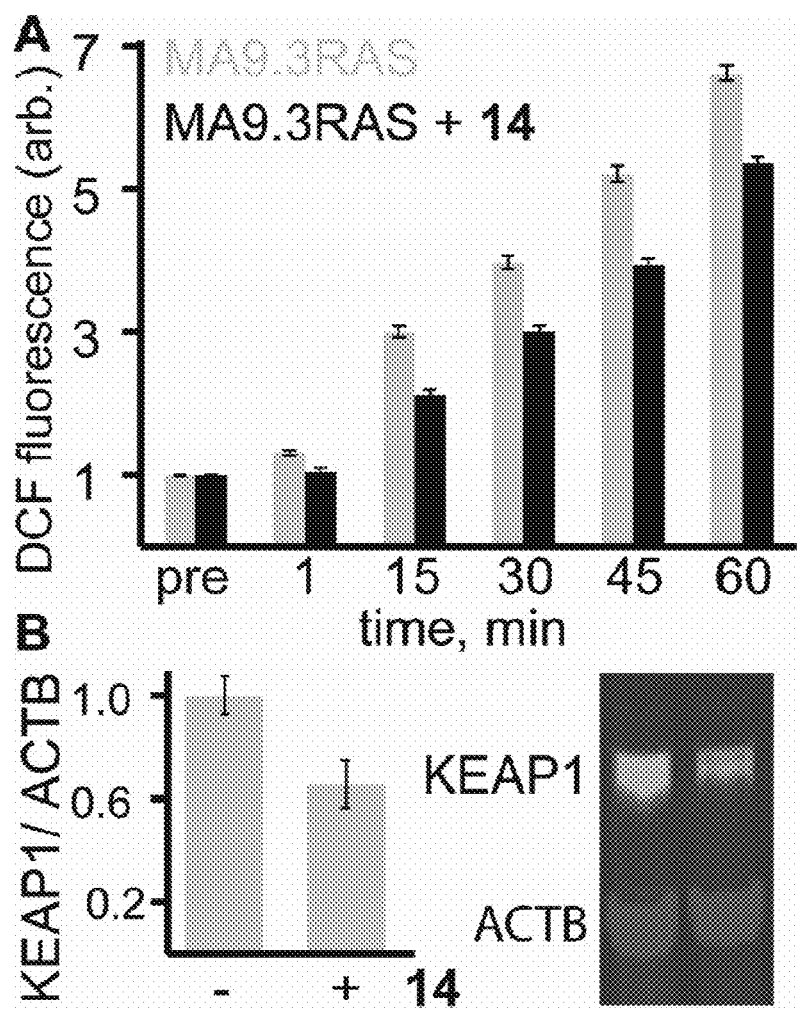
FIG. 8 shows that compound 14 lowers ROS and leads to electrophilic stress.

In order for 14 to be ROS-activatable, it needs to enter a cell and react with hydrogen peroxide, thereby lowering a cell's total ROS level as measured by DCF fluorescence (FIG. 8A). It should be noted that because 14 is highly lethal, concentrations ten-fold higher than the $IC_{50}$ are required to lower a cell's ROS level. When 14 was added to AML cells, the fluorescence intensity was set to 1.06±0.13 and it smoothly increased to 4.31±0.08 over time. Similar experiments lacking addition of 14 show statistically significant increases in fluorescence intensities ($p<0.001$ for all time points while pretreated data set was not statistically significant from each other) with the endpoint having an intensity of 5.02±0.08. Thus, data indicates that 14 enters AML cells and lowers total ROS as it is activated.

Finally, reactivity of 14 in a cell was examined (FIG. 8B). To accomplish this, western blot against KEAP1, normalized to beta-actin was performed. KEAP1 is a signaling molecule that inhibits $NRF2^{25}$, the transcription factor that regulates anti-oxidant concentrations in cells. Loss of KEAP1 is dependent on electrophilic and reactive stressors since it possesses several easy to modify thiols. The data indicates that addition of 14 led to a relative concentration of 0.65±0.09 ($p<0.04$) after 24 hrs.

Example 8

Selectivity of Compound 14

Selectivity of compound 14 was examined by measuring IC$_{50}$ against a variety of cell types, including AML cells obtained from individuals as well as common cell lines and healthy untransformed cells. Results are shown in Table 4 below:

TABLE 4

IC$_{50}$ Data for Compound 14 against a Panel of AML cells vs. Healthy Cells

| Description | Cell Line | IC50 (µM) |
| --- | --- | --- |
| Healthy untransformed cells | UT | 22 ± 2 |
| Individual 1 transformed with MLL-AF9 fusion | A_MA9 | 4 ± 0.7 |
| Individual 1 transformed with MLL-AF9 and FLT3-ITD | A_MA9 + FLT3 | 1.8 ± 0.07 |
| Individual 1 transformed with MLL-AF9 and Nras$^{G12D}$ | A_MA9 + Nras | 2.3 ± 0.08 |
| Individual 2 transformed with MLL-AF9 | B_MA9 | 3.7 ± 0.1 |
| Individual 2 transformed with MLL-AF9 and FLT3-ITD | B_MA9 + FLT3 | 1.6 ± 0.1 |
| Individual 2 transformed with MLL-AF9 and Nras$^{G12D}$ | B_MA9 + Nras | 2.5 ± 0.03 |
| Common AML Cell Line | HL60 | 4 ± 0.09 |
| Common AML Cell Line | MOLM13 | 6 ± 1 |
| Common AML Cell Line | Kasumi1 | 19 ± 3 |

Results show that compound 14 selectively targets AML cells as compared to healthy, untransformed cells.

All documents cited are incorporated herein by reference in their entirety; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A compound according to Formula I:

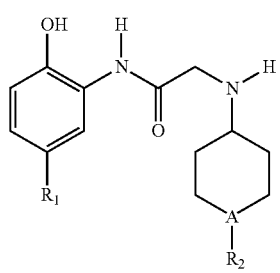

Formula I wherein:
R$_1$ is selected from the group consisting of OH and NHR$_3$, wherein R$_3$ is selected from the group consisting of H and substituted or unsubstituted straight or branched C$_1$-C$_8$ alkyl;
R$_2$ is selected from the group consisting of H, NHR$_4$, C(=O)R$_5$, and substituted or unsubstituted straight or branched C$_1$-C$_8$ alkyl, wherein R$_4$ and R5 are each independently selected from the group consisting of H, substituted or unsubstituted straight or branched C$_1$-C$_8$ alkyl, substituted or unsubstituted straight or branched C$_2$-C$_8$ alkenyl, and substituted or unsubstituted straight or branched C$_2$-C$_8$ alkynyl; and
A is selected from the group consisting of C and N.

2. The compound according to claim 1, wherein R$_1$ is OH.
3. The compound according to claim 1, where R$_1$ is NH$_2$.
4. The compound according to claim 1, wherein A is C and R$_2$ is H.
5. The compound according to claim 1, wherein when A is N, then R$_2$ is C(=O)R$_5$, wherein R$_5$ is selected from the group consisting of H and substituted or unsubstituted methyl, ethyl, propyl, isopropyl, butyl, isobutyl, tert-butyl, pentyl, ethenyl, propenyl, ethynyl, and propynyl.
6. The compound according to claim 1, wherein the cancer is associated with the production of elevated reactive oxygen species (ROS).
7. The compound according to claim 1, wherein the compound is

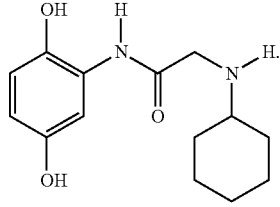

8. A compound selected from the group consisting of:
2-(cyclohexylamino)-N-(2,5-dihydroxyphenyl)acetamide;
N-(5-amino-2-hydroxyphenyl)-2-(1-propioloylpiperidin-4-ylamino)acetamide; and
N-(5-amino-2-hydroxyphenyl)-2-(cyclohexylamino)acetamide.

9. A pharmaceutical composition comprising:
(a) a therapeutically effective amount of a compound according to claim 1; and
(b) a pharmaceutically-acceptable carrier.

10. A method of reducing proliferative capacity in a cell, the method comprising contacting the cell with an effective amount of a compound according to claim 1.

11. The method according to claim 10, wherein the cell is a mammalian cell.

12. The method according to claim 11, wherein the cell is a cancer cell.

13. A method of treating acute myeloid leukemia comprising administering to a subject in need thereof an effective amount of a compound according to claim 1.

14. The method according to claim 13, wherein the subject is a mammal.

15. The method according to claim 13, further comprising administering to the subject one or more additional therapeutic agents.

16. The method according to claim 15, wherein the one or more additional therapeutic agents are selected from the group consisting of cytarabine, doxorubicin, cisplatin, chlorambucil, cladribine, zosuquidar, gemtuzumab, arsenic trioxide, and sorafenib.

17. The method according to claim 16, wherein the one or more additional therapeutic agents are selected from the group consisting of cytarabine and doxorubicin.

* * * * *

UNITED STATES PATENT AND TRADEMARK OFFICE
CERTIFICATE OF CORRECTION

| | |
|---|---|
| PATENT NO. | : 10,071,954 B2 |
| APPLICATION NO. | : 15/026442 |
| DATED | : September 11, 2018 |
| INVENTOR(S) | : Edward J. Merino et al. |

It is certified that error appears in the above-identified patent and that said Letters Patent is hereby corrected as shown below:

In the Specification

In Column 1, Line 13, before the TECHNICAL FIELD, insert:
--STATEMENT REGARDING FEDERALLY SPONSORED RESEARCH OR DEVELOPMENT
This invention was made with government support under R21 CA185370 awarded by the National Institutes of Health. The government has certain rights in the invention.--

Signed and Sealed this
Ninth Day of April, 2024

Katherine Kelly Vidal
*Director of the United States Patent and Trademark Office*